United States Patent
Steier

(10) Patent No.: US 10,598,555 B2
(45) Date of Patent: Mar. 24, 2020

(54) PRESSURE SENSOR, E.G. IN SOLE FOR AN ARTICLE OF FOOTWEAR

(71) Applicant: IEE International Electronics & Engineering S.A., Echternach (LU)

(72) Inventor: Andreas Steier, Pellingen (DE)

(73) Assignee: IEE INTERNATIONAL ELECTRONICS & ENGINEERING S.A., Echternach (LU)

( * ) Notice: Subject to any disclaimer, the term of this patent is extended or adjusted under 35 U.S.C. 154(b) by 0 days.

(21) Appl. No.: 14/406,193

(22) PCT Filed: Jun. 6, 2013

(86) PCT No.: PCT/EP2013/061665
§ 371 (c)(1),
(2) Date: Dec. 5, 2014

(87) PCT Pub. No.: WO2013/182633
PCT Pub. Date: Dec. 12, 2013

(65) Prior Publication Data
US 2015/0177081 A1    Jun. 25, 2015

(30) Foreign Application Priority Data
Jun. 6, 2012    (LU) .......................................... 92 016

(51) Int. Cl.
*G01L 1/20* (2006.01)
*A43B 3/00* (2006.01)
(Continued)

(52) U.S. Cl.
CPC .............. *G01L 1/20* (2013.01); *A43B 3/0005* (2013.01); *A61B 5/1038* (2013.01); *A61B 5/6807* (2013.01); *G01L 1/205* (2013.01)

(58) Field of Classification Search
CPC ..... A43B 3/0005; A43B 313/12; A43B 13/14; A43B 13/122; A43B 13/125;
(Continued)

(56) References Cited

U.S. PATENT DOCUMENTS

| 4,070,544 A | * | 1/1978 | Lambden | ............... | G01B 7/004 |
| | | | | | 178/18.05 |
| 4,745,930 A | | 5/1988 | Confer | | |

(Continued)

FOREIGN PATENT DOCUMENTS

DE    102004055469 A1 *  5/2006 ............. H01H 3/141

OTHER PUBLICATIONS

International Search Report and Written Opinion dated Nov. 19, 2013 re: Application No. PCT/EP2013/061665.

*Primary Examiner* — David J. McCrosky
(74) *Attorney, Agent, or Firm* — Reising Ehtington P.C.

(57) ABSTRACT

A pressure sensor, e.g. for being arranged in the sole structure of an article of footwear, for measuring a pressure exerted by the wearer's foot. The pressure sensor has one or more pressure-sensing cells. Each cell has a first flexible carrier film and a second flexible carrier film, the first and second carrier films being attached to one another by a spacer film having an opening, a plurality of first electrodes arranged on the first carrier film and a plurality of second electrodes arranged on the second carrier film. The plurality of first electrodes has a first group of electrodes and a second group of electrodes. The first and second groups of electrodes are arranged so as to interdigitate with delimiting gaps there between. One or more electrically insulating overprints are arranged on the first carrier film so as to cover the gaps.

18 Claims, 6 Drawing Sheets

(51) Int. Cl.
*A61B 5/103* (2006.01)
*A61B 5/00* (2006.01)

(58) Field of Classification Search
CPC ... A43B 17/1405; A43B 13/386; A43B 7/084;
A43B 7/087; A43B 7/088; A61B 5/6807
See application file for complete search history.

(56) References Cited

U.S. PATENT DOCUMENTS

| | | | |
|---|---|---|---|
| 4,822,957 A * | 4/1989 | Talmage, Jr. | G06F 3/045 |
| | | | 178/18.05 |
| 9,089,182 B2 * | 7/2015 | Schrock | A61B 5/6807 |
| 9,549,585 B2 * | 1/2017 | Amos | A43B 3/0005 |
| 2004/0163939 A1 | 8/2004 | Bieck et al. | |
| 2008/0018608 A1 * | 1/2008 | Serban | G06F 3/0416 |
| | | | 345/173 |
| 2010/0063779 A1 | 3/2010 | Schrock | |
| 2010/0313680 A1 | 12/2010 | Joung et al. | |
| 2013/0213147 A1 * | 8/2013 | Rice | A43B 3/0005 |
| | | | 73/862.046 |
| 2014/0033572 A1 * | 2/2014 | Steier | A43B 3/0005 |
| | | | 36/103 |

\* cited by examiner

B-B

PRESSURE SENSOR, E.G. IN SOLE FOR AN ARTICLE OF FOOTWEAR

TECHNICAL FIELD

The present invention generally relates to a pressure sensor, especially but not exclusively for an article of footwear, such as e.g. a shoe, a boot, a sandal or the like. Such a pressure sensor may be used for measuring pressure exerted by the wearer's foot on the sole structure.

BACKGROUND ART

Document US 2010/0063779 discloses a shoe with an integrated sensor system. The sensor system collects performance data that are transferred for further use via a communication port. The shoe contains a force sensor arranged in the sole structure for measuring, in a plurality of areas, pressure (force) exerted by the wearer's foot on the sole structure, and an electronic module configured to gather data from the sensors. The module is configured for transmitting the data to an external device for further processing. In one of the embodiments disclosed in US 2010/0063779, the pressure sensor comprises four elongated pressure-sensing cells, each of which contains a first and a second electrode as well as a force-sensitive resistive material disposed between the electrodes to electrically connect the electrodes together. When pressure is applied to the force-sensitive material, its resistivity changes, and the resulting change in resistance is detected by the electronic module. Materials exhibiting volume-based resistance behavior are used as the force-sensitive material: when such material is compressed, conductive particles contained therein move closer together, whereby conductive paths are formed and the resistance decreases. If another resistance vs. pressure characteristic is needed, a suitable force-sensitive material has to be found, which may be difficult.

BRIEF SUMMARY

The invention provides a pressure sensor, wherein the one or more pressure sensing cells have an increased dynamic range, i.e. whose electrical resistance decreases more slowly with increasing pressure but over a broader range.

The proposed pressure sensor comprises one or more pressure-sensing cells. Each cell comprises a first flexible carrier film and a second flexible carrier film, the first and second carrier films being attached to one another by a spacer film having an opening, a plurality of first electrodes arranged on the first carrier film and a plurality of second electrodes arranged on the second carrier film, the plurality of first electrodes and the plurality second electrodes being arranged in facing relationship with each other in the opening in such a way that the first and second electrodes may be brought into contact with one another when pressure is exerted on the pressure-sensing cell and that contact areas between the first and second electrodes increase with increasing pressure. The first electrodes are resistive electrodes (e.g. made of graphite ink, carbon ink, graphite-carbon ink or the like). The plurality of first electrodes comprises a first group of electrodes and a second group of electrodes, the first and second groups of electrodes being arranged so as to interdigitate while delimiting gaps there between. The first carrier film carries conductive tracks that contact border portions of the first electrodes, which extend along the gaps, each conductive track defining an equipotential line in the respective border portion. One or more electrically insulating overprints are arranged on the first carrier film so as to cover the gaps. The overprints at least partially overlap with (preferably completely cover) the border portions in which the first electrodes are contacted by the conductive tracks. The electrically insulating overprints locally prevent a direct contact between the first and second electrodes and enable the direct contact where they are absent. The pressure sensor according to the invention may especially (but not exclusively) be used in an article of footwear (in particular a sports shoe, such as e.g. a running shoe, a tennis shoe or the like) that comprises a sole structure for supporting a wearer's foot and an upper for holding the wearer's foot onto the sole structure. In this case, a pressure sensor according to the invention is preferably arranged in the sole structure for measuring a pressure exerted by the wearer's foot on the sole structure.

The above-described pressure-sensing cell exhibits an improved dynamic response due to the presence of the electrically insulating overprints and the conductive tracks in the border regions of the first electrodes. These layers locally reinforce the first carrier film, whereby the mechanical response of the carrier film is shifted to higher pressures (i.e. it bends less easily under pressure). It follows that the rate of growth of the contact area between the first and second electrodes decreases with increasing pressure (at higher pressures, the contact area spreads towards the borders of the pressure-sensitive cell, where at least the first carrier film yields less easily under pressure due to the presence of the conductive track and the overprints). This means, in turn, that maximum mechanical contact between the first electrodes and the second electrodes occurs at a higher pressure than in conventional pressure sensing cells.

Preferably, the pressure-sensing cells are configured (in particular by tailoring of the shape of the electrically insulating overprints) in such a way that pressures in the range from about 0.1 bar to 7 bar translate into a steady change of the contact area between the resistive electrodes (and thus of the electrical resistance of the cell) from 0% (at the turn-on pressure, i.e. at the about 0.1 bar) and about 100% (full contact at about 7 bar).

Preferably, also the second electrodes are resistive electrodes. Alternatively, they can be conductive electrodes (e.g. made of a silver ink or a conductive carbon/graphite ink). The electrically insulating overprints are preferably made of electrically insulating (dielectric) ink.

Advantageously, the plurality of second electrodes comprises a third group of electrodes and a forth group of electrodes, the third and second fourth groups of electrodes being arranged so as to interdigitate while delimiting gaps there between. Most preferably, the first and second electrodes are mirror-symmetrical to each other.

Also the second carrier film may carry conductive tracks that contact border portions of the second electrodes extending along the gaps.

The third and fourth groups of electrodes may be separated from each other by a high impedance when the first and second electrodes are not in contact with one another and shunted via the first electrodes when the first and second electrodes are in contact with one another. Additionally or alternatively, the first and second groups of electrodes may be separated from each other by a high impedance when the first and second electrodes are not in contact with one another and shunted via the second electrodes when the first and second electrodes are in contact with one another.

Preferably, the one or more sensor cells of a pressure sensor to be arranged in a sole structure of an article of footwear are located in areas expected to be subjected to pressure peaks when the wearer of the footwear is standing still, is walking or is running. Advantageously, each of the one or more sensor cells is preferably located in an area corresponding to a bone or part of bone of a wearer's foot selected from the heel bone, the head of the first metatarsal bone, the head of the fourth or fifth metatarsal bone, the head of the second or third metatarsal bone and the head of the first phalange. Those skilled will appreciate that pressure maxima are typically located under the heel bone, under the heads of the fourth and/or fifth metatarsal bone and under the head of the first phalange when the wearer is standing at rest; when the wearer is walking, the pressure maxima are usually under the heel bone, under the heads of the second and/or third metatarsal bone and under the head of the first phalange.

The pressure-sensing cells may have various shapes. For instance, each of the pressure-sensing cells may be oval, elliptical or rectangular with rounded angles.

For equalization of gas pressure inside the opening, each of the pressure sensing cells advantageously comprises a ventilation hole. The ventilation hole may be in fluid communication with the exterior of the pressure sensor (e.g. the atmosphere) or with a gas (e.g. air) reservoir within the pressure sensor. Such gas reservoir could e.g. be a cavity between the first and second carrier films.

According to a preferred embodiment of the invention, the pressure sensor comprises a foam rubber support, e.g. made of ethylene vinyl acetate (EVA), preferably fixed to the first or the second carrier film by means of an adhesive.

As those skilled will appreciate, the pressure sensor could be arranged in different parts of a sole structure of footwear. For instance, the pressure sensor could be arranged on or in the insole. Alternatively, the pressure sensor could be arranged on, in or under the midsole.

Another aspect of the present invention relates to a pressure sensor for an article of footwear that comprises a flexible multilayer film structure, wherein the pressure sensor further comprises a trough-shaped receptacle for an electronic control module, the receptacle comprising in its interior a plurality of connection pins for interfacing the pressure sensor with the electronic control module. Preferably, the trough-shaped receptacle is made of plastic material, e.g. PET or epoxy.

The receptacle is preferably arranged in an opening provided in the flexible multilayer film structure. The receptacle may comprise a bottom part and a top part, the bottom part and the top part being assembled with each other so as to squeeze between each other a border of the opening in the multilayer film structure and thus securing the multilayer film structure to the receptacle.

BRIEF DESCRIPTION OF THE DRAWINGS

Preferred, non-limiting, embodiments of the invention will now be described, by way of example, with reference to the accompanying drawings in which.

DESCRIPTION OF PREFERRED EMBODIMENTS

Figure 1:
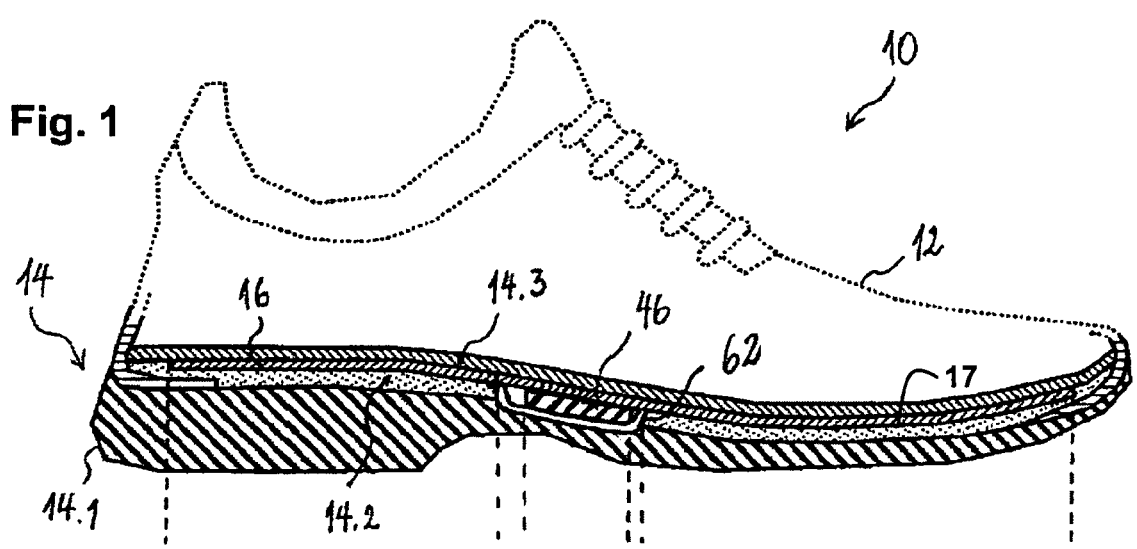
FIG. 1 is a longitudinal cross sectional view of the sole structure of a sports shoe equipped with a pressure sensor in accordance with a preferred embodiment of the invention.

An article of footwear, in form of a sports shoe 10 is depicted in FIG. 1 as including an upper 12 and a sole structure 14. The upper 12 is secured to sole structure 14 and defines a chamber for receiving a foot. The sole structure 14 includes an outsole 14.1, a midsole 14.2, and an insole 14.3, which forms the bottom of the foot-receiving chamber of the sport shoe 10.

The film-type pressure sensor is arranged on the upper surface of an EVA substrate 17. In the illustrated embodiment, the midsole 14.2, which is preferably formed of impact-attenuating material, has the film-type pressure sensor 16 on its substrate 17 attached to its upper surface. When the insole is in place, the pressure sensor 10 is thus sandwiched between the insole 14.3 and the midsole 14.2.

Figure 2:
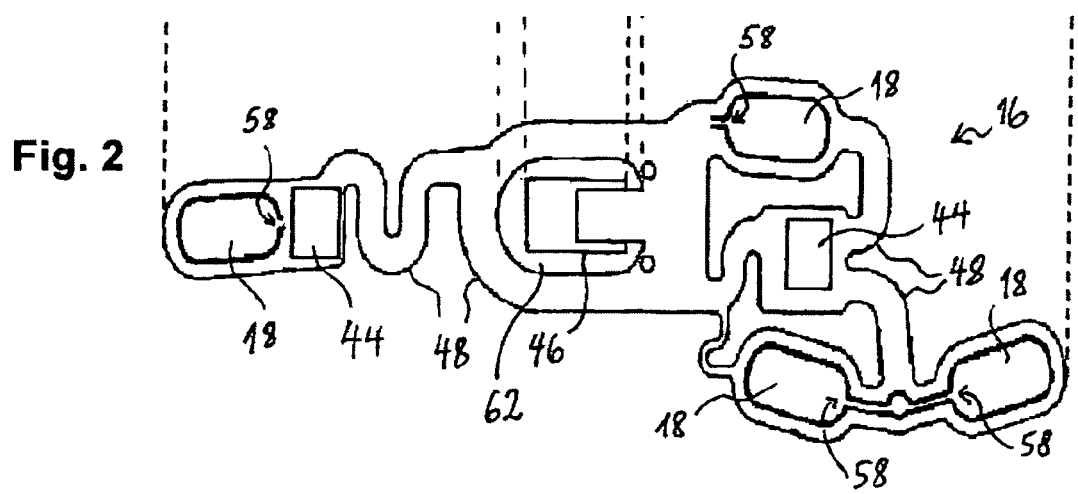
FIG. 2 is a top view of the pressure sensor of the sports shoe of FIG. 1.

As best shown in FIG. 2, the pressure sensor 16 comprises a plurality of pressure-sensing cells 18, located in different areas of the sole structure 14, for measuring pressure exerted by the wearer's foot on the sole structure 14.

Figure 4:
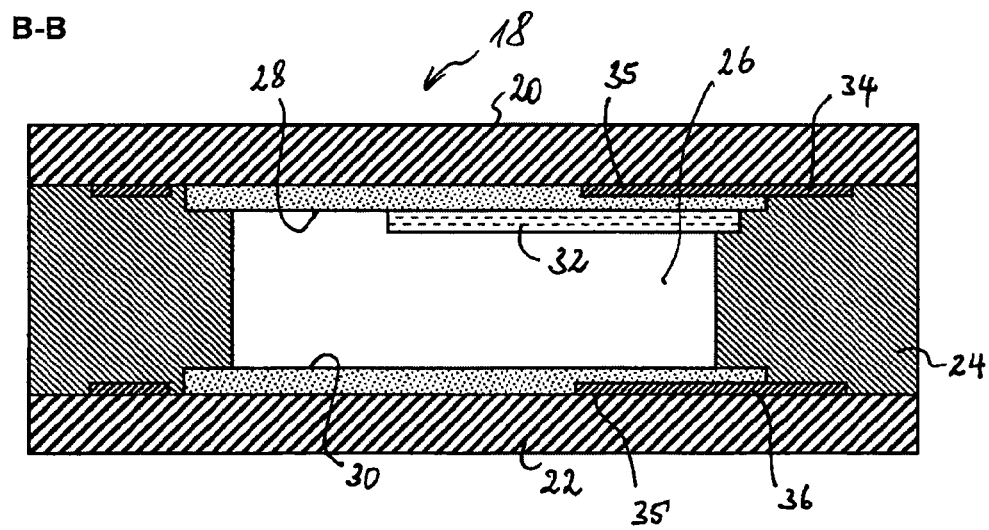
FIG. 4 is a schematic cross sectional view of the B-B plane of FIG. 3.
Figure 3:
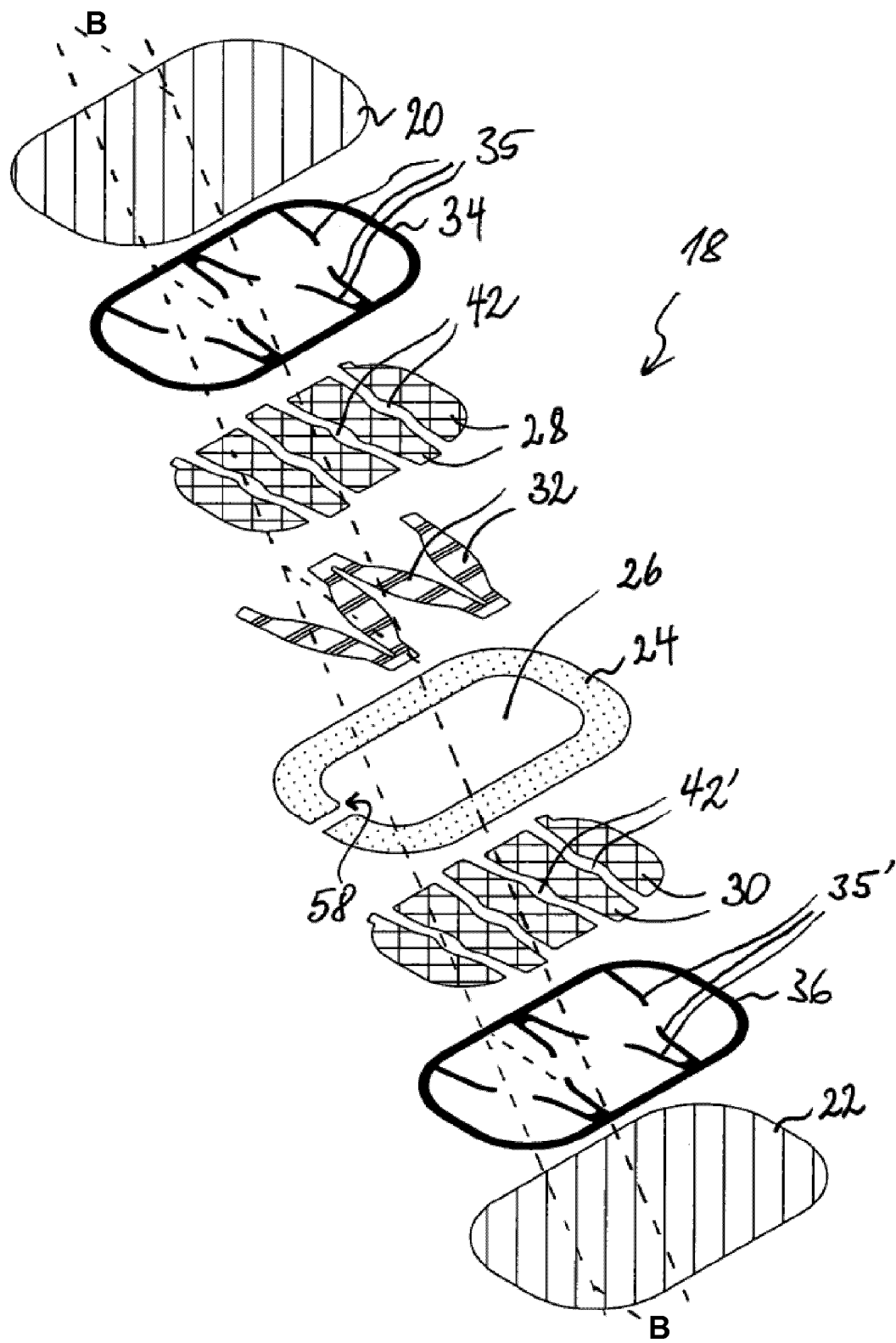
FIG. 3 is an exploded view of one of the pressure-sensing cells of the pressure sensor of FIG. 2.

The configuration of the pressure sensing cells 18 will now be described with reference to FIGS. 3 and 4. FIG. 3 shows the different layers of a pressure-sensing cell 18. FIG. 4 shows the pressure-sensing cell of FIG. 3 in cross section. The pressure sensor 16 comprises a multilayered structure including a first carrier film 20, a second carrier film 22, and a spacer 24. The spacer 24 is typically a double-sided adhesive, with which the first and second carrier films 20, 22 are laminated together. The first and second carrier films 20, 22 are preferably made of PET but other materials such as PEN, PI, PEEK etc. are also possible. Each of the carrier films may comprise a single film layer or comprise a plurality of film layers of the same or different materials. The spacer 24 preferably comprises a PET, PEN, PI, PEEK, etc. film layer with an adhesive coating applied on each side thereof. At each pressure-sensing cell 18, the spacer comprises an oblong opening 26, within which the first and second carrier films 20, 22 may be pressed together. In each pressure-sensing cell 18, a plurality of first, resistive, electrodes 28 is printed on the first carrier film 20 and a plurality of second electrodes 30 is printed on the second carrier film 22, in facing relationship with the a plurality of first electrodes 28. Each plurality of electrodes 28, 30 is contacted by a respective conductive track 34, 36. The plurality of first electrodes 28 is partially covered with electrically insulating overprints 32 (made e.g. of a dielectric ink), in such a way as to locally prevent a direct contact between the electrodes on the first carrier film 20 and those on the second carrier film 22.

As best illustrated in FIG. 3, the plurality of first electrodes 28 comprises a first group of electrodes and a second group of electrodes arranged so as to interdigitate while delimiting gaps 42 there between. The electrodes of each group contact the conductive track 34 only on one longitudinal side of the pressure-sensitive cell 18. The conductive track 34 comprises studs 35 arranged in contact with border portions of the first electrodes 28 that extend along the gaps 42. Likewise, the plurality of second electrodes 30 comprises a third group of electrodes and a second group of electrodes arranged so as to interdigitate while delimiting gaps 42' there between. The electrodes of each group contact the conductive track 36 only on one longitudinal side of the pressure-sensitive cell 18. The conductive track 36 comprises studs 35' arranged in contact with border portions of the second electrodes 30 that extend along the gaps 42'.

In response to pressure acting on the pressure-sensing cell 18, at least one of the first and second carrier films 20, 22, deflects towards the other carrier film until the carrier films 20, 22 or the elements on their respective surface come into contact. FIG. 10 illustrates the evolution of the mechanical contact areas on the second carrier film 22. Contours 64, 64' and 64" represent the contact areas as pressure on the pressure-sensing cell increases. Once contact is established (inner contours 64), the radius of the mechanical contact areas increases (see arrows 66) with increasing pressure. When a direct contact is established between the electrodes 28 and 30, the electrical resistance between the conductors 34 and 36 becomes finite and a current may flow in consequence. As the contact area between the first and second electrodes 28, 30 increases, the resistance measurable between the conductors 34 and 36 decreases. The positions of the contacts between the resistive electrodes 28, 30 and the respective conductive trace 34, 36, the specific resistance of the resistive electrodes, the shape of the first and second electrodes 28, 30, the shape of the electrically insulating overprints 32 and the mechanical properties of the carrier films 20, 22 determine the pressure-dependent cell resistance. Referring to the cell configuration of FIGS. 3, 9 and 10, the first and second electrodes 28, 30 have a roughly equal-sided triangular shape. The base of the triangles extends substantially parallel to the longitudinal axis of the pressure-sensing cell. Each electrode 28, 30 is contacted with the conductive studs 35, 35' at the tip opposite the base. The initial contact (contours 64) between the first and second electrodes 28, 30 occurs approximately at the center of each triangle. The dielectric overprints 32 on the first electrodes 28 (shown as a dashed line in FIG. 10) prevent that a single, continuous contact area is formed. Each contact area grows as roughly shown by arrows 66 when pressure increases. When the contact area has reached a certain size, the residual resistance between the conductors 34 and 36 is mainly due to the resistive path between the contact areas and the conductive studs 35, 35'. (The resistance of the conductive tracks and the studs may be neglected.) At higher pressures, each contact area grows into the region between the studs 35, 35', which tapers in the direction of the tip of the triangle. Since the dielectric overprints 32 locally maintain the carrier films 20, 22 at a certain minimum distance from each other, the rate of growth of the contact area decreases as the contact area enters the region between the studs 35, 35'.

The electrical response function of the pressure-sensing cells, i.e. the resistance versus pressure, may be adjusted in a predetermined manner by suitably shaping the overprints 32, because the electrically overprints 32 locally prevent a direct contact between the first and second electrodes 28, 30 whereas the direct contact is possible in those areas where the electrically insulating overprints 32 are absent.

Figure 5:
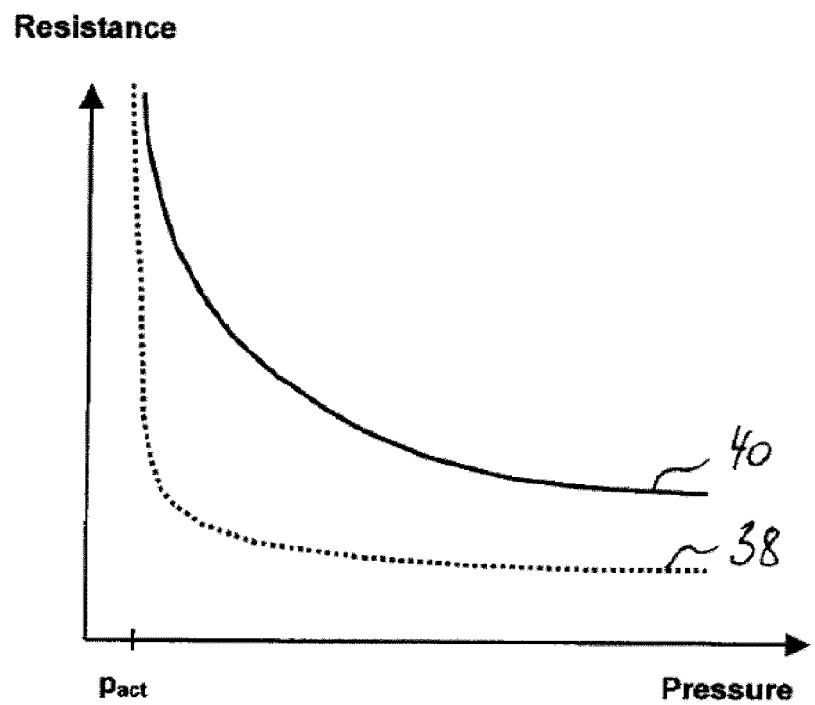
FIG. 5 is a graph illustrating the difference in the electrical responses of a pressure-sensing cell without an electrically insulating overprints and one with such overprints.

FIG. 5 schematically illustrates the difference in the electrical response of a pressure-sensing cell without the overprints (dotted curve 38) and one with the overprints shaped as in FIG. 3 (continuous curve 40), all other cell parameters being the same. One notes that for the pressure-sensing cell without the insulating overprints the resistance change occurs in a relatively small pressure range starting at the activation pressure $p_{act}$ (the pressure at which the electrodes enter into contact). Above $p_{act}$, the resistance quickly levels out at a low value. For the cell equipped with the insulating overprints, the resistance change spreads over a significantly longer pressure interval. As a consequence, the cell with the insulating overprints enables pressure measurement at significantly higher pressures than the cell without the insulating overprints. It shall be noted that the conductive studs 35, 35' and the insulating overprints 32 also locally reinforce the carrier films 20, 22. The suppleness of the carrier films 20, 22 is thus locally reduced, which means that, in vicinity of the conductive studs and the insulating overprints, more pressure is needed to bring the first and second electrodes into contact, which increases the dynamic range of the sensor.

As best illustrated in FIG. 2, the pressure-sensing cells 18 are arranged in areas of the shoe 10, in which the pressure peaks are expected to occur when the wearer is standing, walking or running. Specifically, a first one of the pressure-sensing cells is positioned in the area of the head of the first phalange (big toe), a second one in the area of the head of the first metatarsal bone, a third one in the area of the head of the fifth metatarsal bone and a fourth one in the area of the calcaneum (heel bone).

For fixation of the pressure sensor 16 to the sole structure 14 (in this example the midsole), the pressure sensor 16 comprises one or more fixation pads 44 (see FIG. 2). The fixation pads 44 preferably comprise a layer of pressure-sensitive or heat-activatable adhesive, initially protected by a release liner, which is removed just before the pressure sensor 16 is attached to its carrier member of the sole structure 14. Instead of using local fixation pads 44, the entire surface of the first 20 or the second 22 carrier film can be coated with an adhesive (and initially protected by a release liner).

The pressure sensor 16 further comprises an electronic control module 46, which is arranged within a trough-shaped receptacle 62 and mechanically attached to the multilayer film structure of the pressure-sensor 10. Connection strips 48 interconnect the pressure sensing cells 18 and the electronic control module 46. The connection strips 48 are integral part of the multilayer film structure of the pressure sensor 16 and carry conductive tracks that electrically connect the first and second electrodes of each pressure-sensing cell 18 with the electronic control module 46. The connection strips 48 may have a serpentine shape to act as springs and to thereby increase the pressure-sensor's elasticity in the sensor plane.

The electronic control module 46 preferably comprises an application-specific integrated circuit (ASIC), a field-programmable gate array (FPGA), a microprocessor, or the like. Advantageously, the electronic control circuit is configured for wirelessly transmitting the collected pressure data or any data derived there from to a receiver appliance having a user interface. Such receiver appliance could include a (wrist-) watch, the wrist receiver of a heart rate monitor, a handheld computer, a mobile phone, a portable media player or the like. In the illustrated embodiment, the electronic control module 46 is arranged in a cavity or well of the midsole 14.2.

The cavity or well may be located elsewhere in the sole structure 14 in other embodiments.

For equalization of gas pressure inside the opening 26 of the spacer 24, each pressure-sensing cell 18 comprises a ventilation hole 58 (best shown in FIGS. 2 and 3). The ventilation holes 58 fluidly connect the interiors of the pressure sensing cells to the outside, so that compression of the gas inside the pressure sensing cells is essentially avoided and thus has no significant impact on the response curve of each cell 18. Additionally or alternatively, the ventilation holes 58 could be connected to a gas reservoir within the film-type pressure sensor.

Figure 6:
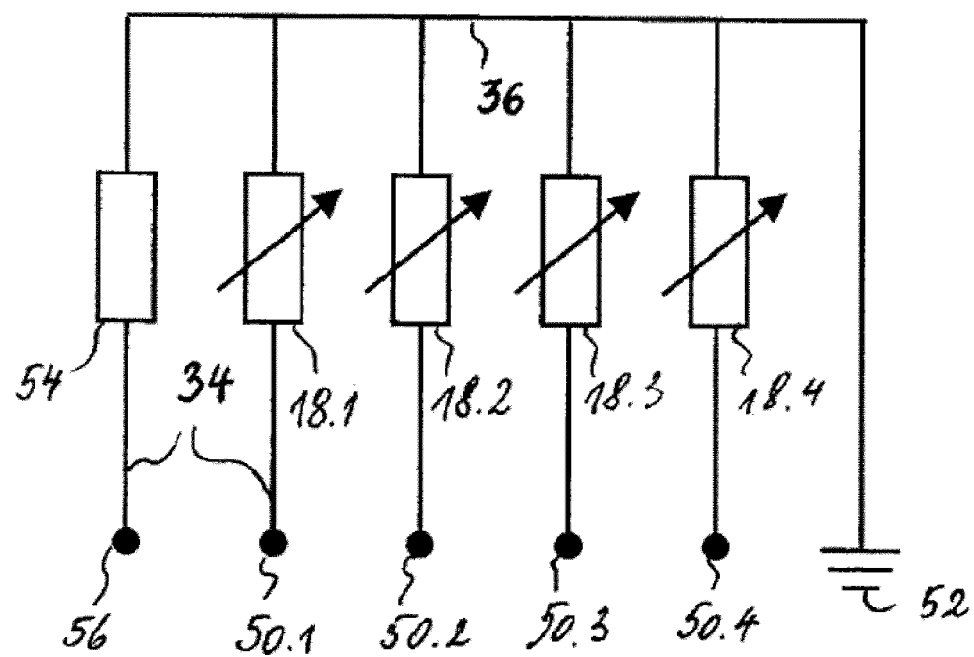
FIG. 6 is a block diagram of the electrical circuit of the pressure sensor illustrated in FIG. 2.

FIG. 6 is a schematic block diagram of the flexible circuit of the pressure sensor 16. The pressure-sensing cells 18 are drawn as variable resistors 18.1-18.4. The cells are arranged electrically in parallel between a respective terminal 50.1, 50.2, 50.3 or 50.4 of the electronic control module (not shown in FIG. 6) and circuit ground 52. The electronic control module determines the pressure values based upon the resistance (or the current or the voltage if one of these quantities is kept constant) measured between each terminal 50.1, 50.2, 50.3 or 50.4 and circuit ground. It should be noted that the cell response curve is influenced by changes in resistivity of the electrode material, which may vary depending on ageing, temperature, humidity or other environmental influences. To be able to correct or compensate such influence on the pressure values, a reference resistor 54 is provided. The reference resistor 54 is made of the same material as the electrodes 28, 30. It is arranged somewhere on the pressure sensor 16 so that it experiences essentially the same environmental influences as the electrodes 28, 30. In the illustrated embodiment, the reference resistor 54 is arranged electrically between a reference terminal 56 and circuit ground 52, in parallel to the pressure sensing cells. The electronic control module measures the resistance of the reference resistor 54. Any deviation from a nominal value is used to correct the readings of the pressure-sensing cells 18. The reference resistor 54 may be arranged on either one of the carrier films 20, 22. One could also use a plurality of resistors arranged on one or both of the carrier films. Another possibility would be to provide a preloaded pressure-sensing cell (i.e. a pressure-sensing cell wherein the electrodes are permanently kept in contact).

The reference resistor 54 and the resistive electrodes 28, 30 of the pressure-sensing cells are preferably obtained by printing of carbon ink on the respective carrier film. The conductive tracks 34, 36 (including studs 35 and 35') are preferably made of silver ink.

Figure 7:
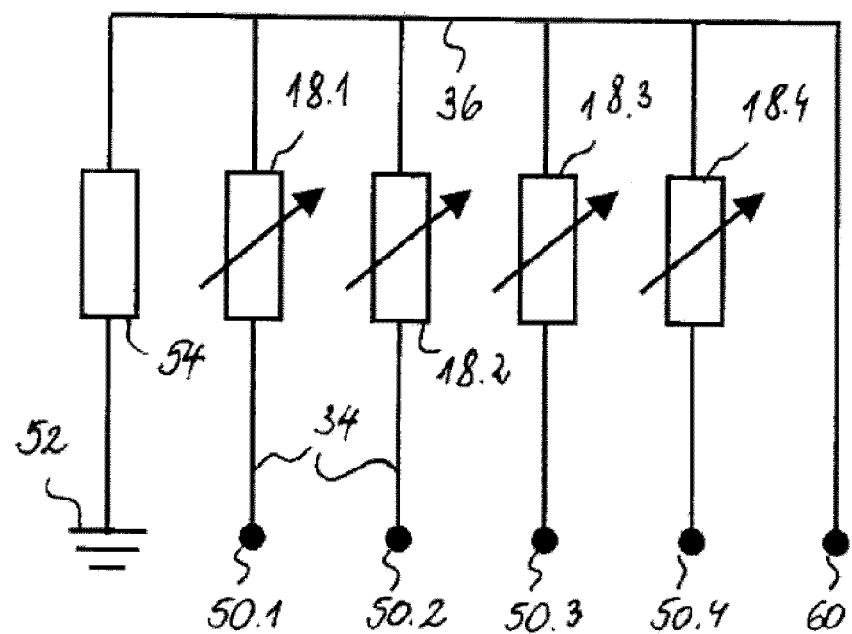
FIG. 7 is a schematic block diagram of an alternative electrical circuit for the pressure sensor of FIG. 2.

FIG. 7 is a schematic block diagram of an alternative flexible circuit for the pressure sensor 16. Unlike in the flexible circuit of FIG. 6, the reference resistor 54 is arranged electrically between circuit ground 52 and the pressure-sensing cells 18, drawn again as variable resistors 18.1-18.4, in the manner of a voltage divider. During the measurement, one pressure-sensing cell at a time may be connected to a voltage source (e.g. a battery) by means of its terminal 50.1, 50.2, 50.3 or 50.4. The electronic control module determines the pressure values based upon the voltages measured on measurement terminal 60. The resistance $R_x$ of one of the pressure-sensing cells 18.1-18.4 may be obtained by $R_x = R_{ref}(U_0/U_{meas}-1)$, where $R_{ref}$ is the resistance of the reference resistor, $U_0$ the voltage applied at the terminal 50.1, 50.2, 50.3 or 50.4, and $U_{meas}$ the voltage measured at the terminal 60. As one supposes that the resistances of the pressure-sensing cells and the reference resistors are subjected to the same changes due to environmental influences (temperature, ageing, etc.), the normalized resistance $R_x/R_{ref}$ is essentially independent of these effects. In all other respects, the circuit for the pressure sensor 16 of FIG. 7 is configured and operates in the same way as the one of FIG. 6.

Figure 8:
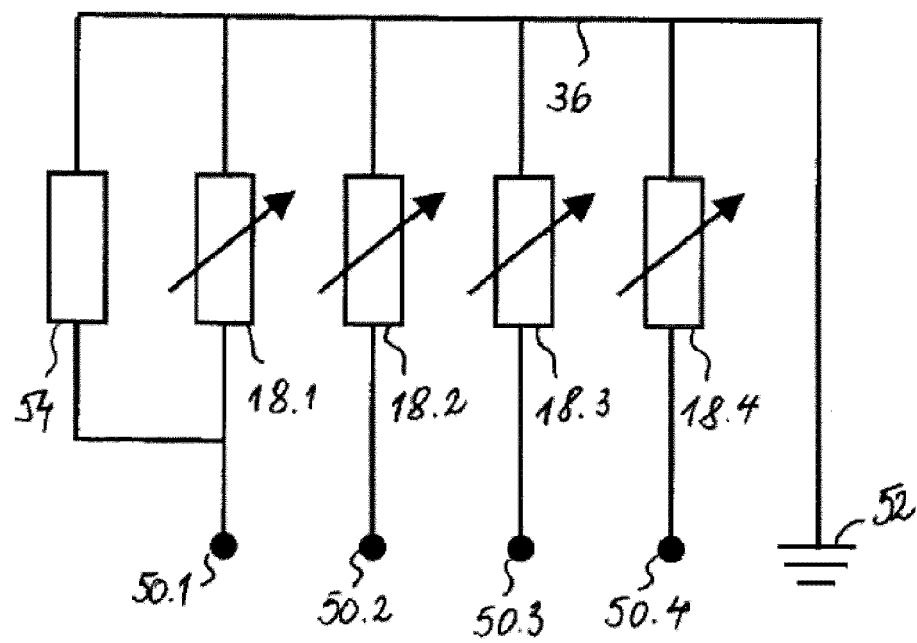
FIG. 8 is a schematic block diagram of another alternative electrical circuit for the pressure sensor of FIG. 2.

FIG. 8 is a schematic block diagram of another alternative flexible circuit for the pressure sensor 16. According to this alternative, the reference resistor 54 is arranged in parallel with one of the pressure-sensing cells 18.1-18.4. In this arrangement, the reference resistance is substantially higher than the resistances of the pressure-sensing cells 18.1-18.4 in actuated state (i.e. above the activation pressure).

Figure 9:
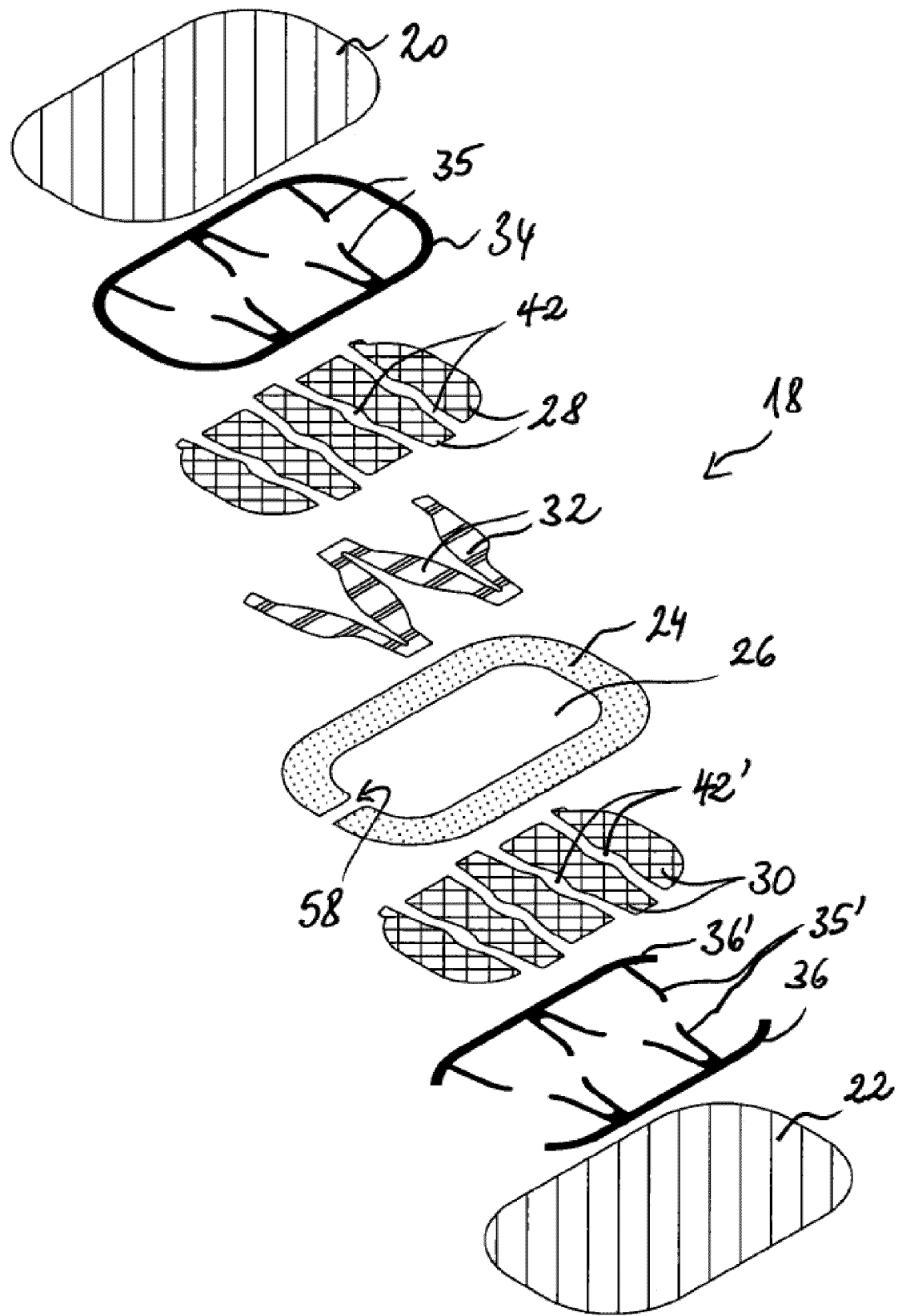
FIG. 9 is an exploded view of a variant of the pressure-sensing cell of FIG. 3.
Figure 10:
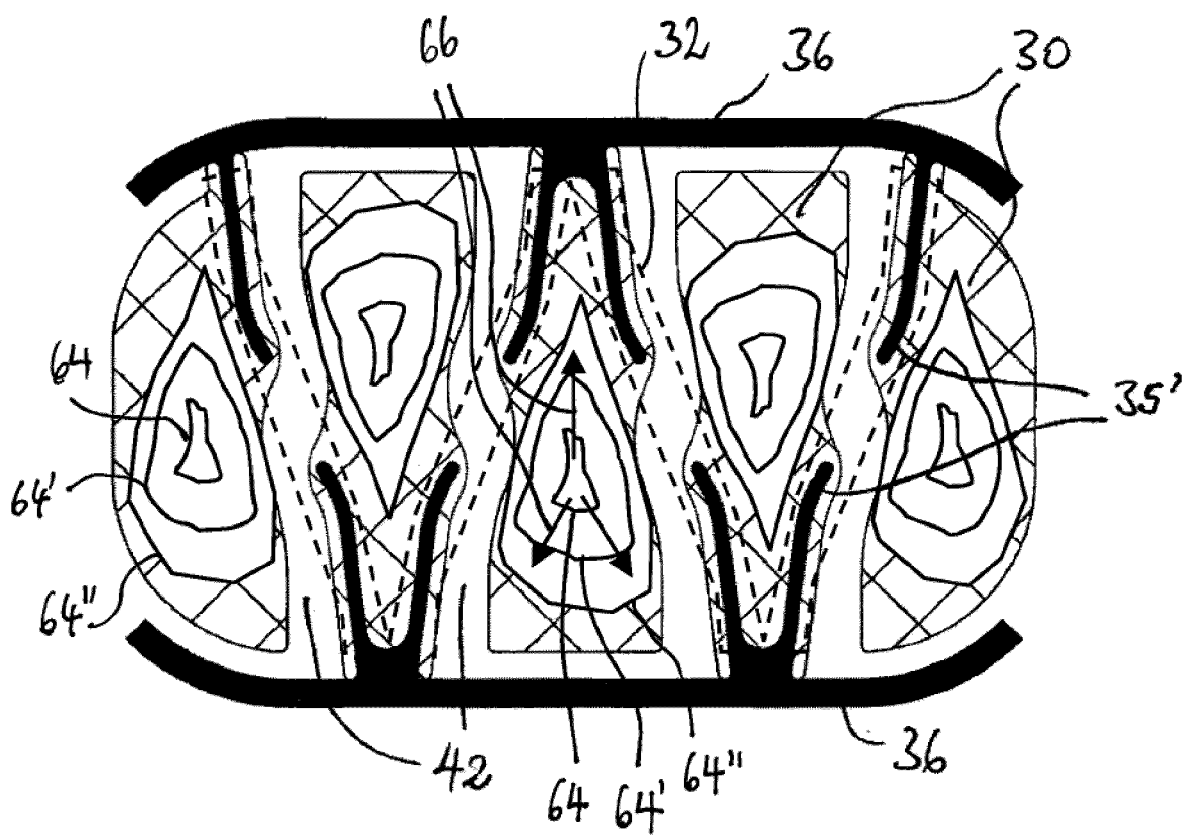
FIG. 10 is an illustration of the pressure-dependent growth of the contact areas between the electrodes of a pressure-sensing cell as shown in FIG. 3 or 9.

FIG. 9 shows a variant of the pressure-sensitive cell 18 of FIG. 3. The only difference with respect to FIG. 3 is that the third and fourth groups of second electrodes 30 are contacted by separate conductive tracks 36, 36'. The third and fourth groups of electrodes are thus separated from each other by a high impedance when the first and second electrodes are not in contact with one another. They are shunted via the first electrodes when the first and second electrodes are in contact with one another. The electrical resistance of the cell is measured between the conductive tracks 36 and 36'. The pressure-sensitive cell is, therefore, of the so-called "shunt-mode" type. (In contrast, the cell of FIG. 3 is said to be of the "through-mode" type; the electrical resistance is measured between the conductive traces 34 and 36.). The first carrier film 20 may also carry separate conductive tracks that contact border portions of the first electrodes 28 extending along the gaps, each of the conductive tracks defining an equipotential line, and wherein one or more electrically insulating overprints are arranged on the first carrier film 20 so as to cover the gaps. The overprints at least partially overlap with the border portions in which the first electrodes are contacted by the conductive tracks.

While specific embodiments have been described in detail, those with ordinary skill in the art will appreciate that various modifications and alternatives to those details could be developed in light of the overall teachings of the disclosure. Accordingly, the particular arrangements disclosed are meant to be illustrative only and not limiting as to the scope of the invention, which is to be given the full breadth of the appended claims and any and all equivalents thereof.

The invention claimed is:

1. A pressure sensor comprising one or more pressure-sensing cells, each of said pressure sensing cells comprising:
    a first flexible carrier film and a second flexible carrier film, said first and second carrier films being attached to one another by a spacer film having an opening; and
    a plurality of first electrodes arranged on said first carrier film and a plurality of second electrodes arranged on said second carrier film, said plurality of first electrodes and said plurality second electrodes being arranged in facing relationship with each other in said opening in such a way that said first and second electrodes may be brought into contact with one another when pressure is exerted on said pressure-sensing cell and that contact areas between said first and second electrodes increase with increasing pressure,
    wherein said first electrodes are resistive electrodes,
    wherein said plurality of first electrodes comprises a first group of electrodes and a second group of electrodes, said first and second groups of electrodes being arranged so as to interdigitate while delimiting gaps there between,
    wherein said plurality of second electrodes comprises a third group of electrodes and a fourth group of electrodes, said third and fourth groups of electrodes being arranged so as to interdigitate while delimiting gaps there between, wherein said first and second carrier films carry a conductive track that includes stud portions configured to contact border portions of said first and second electrodes, wherein the border portions extend along said gaps between said first and second groups of electrodes and along said gaps between said third and fourth group of electrodes, each of the conductive track stud portions defining an equipotential line in the respective border portions, wherein one or more electrically insulating overprints are arranged on said first carrier film so as to cover said gaps between said plurality of first electrodes, said overprints at least partially overlapping with the border portions between said first and second groups of electrodes in which said first electrodes are contacted by said conductive tracks, and wherein a pressure-dependent cell resistance of said pressure-sensing cell is based on a size and/or shape of the one or more electrically insulating overprints.

2. The pressure sensor as claimed in claim 1, wherein said second electrodes are resistive electrodes.

3. The pressure sensor as claimed in claim 1, wherein said third and fourth groups of electrodes are separated from each other by a high impedance when said first and second electrodes are not in contact with one another and wherein said third and fourth groups of electrodes are shunted via said first electrodes when said first and second electrodes are in contact with one another.

4. The pressure sensor as claimed in claim 1, wherein said third and fourth groups of electrodes are separated from each other by a high impedance when said first and second electrodes are not in contact with one another and wherein said third and fourth groups of electrodes are shunted via said first electrodes when said first and second electrodes are in contact with one another.

5. The pressure sensor as claimed in claim 1, wherein said first and second groups of electrodes are separated from each other by a high impedance when said first and second electrodes are not in contact with one another and wherein said first and second groups of electrodes are shunted via said second electrodes when said first and second electrodes are in contact with one another.

6. The pressure sensor as claimed in claim 1, wherein said pressure sensor is configured for being arranged in a sole structure of an article of footwear in order to measure a pressure exerted by a wearer's foot on the sole structure, wherein said one or more sensor cells are located in areas expected to be subjected to pressure peaks when the wearer is standing still, is walking or is running.

7. The pressure sensor as claimed in claim 6, wherein each of said one or more sensor cells is located in an area corresponding to a bone or part of bone of a wearer's foot selected from the heel bone, the head of the first metatarsal bone, the head of the fourth or fifth metatarsal bone, the head of the second or third metatarsal bone and the head of the first phalange.

8. The pressure sensor as claimed in claim 1, wherein each of said pressure sensing cells is oval, elliptical or rectangular with rounded angles.

9. The pressure sensor as claimed in claim 1, wherein each of said pressure sensing cells comprises a ventilation hole for equalization of gas pressure inside said opening.

10. The pressure sensor as claimed in claim 9, wherein said ventilation hole is in communication with an exterior or a gas reservoir.

11. The pressure sensor as claimed in claim 1, further comprising a foam rubber support.

12. The pressure sensor as claimed in claim 11, wherein said foam rubber support is made of ethylene vinyl acetate.

13. The pressure sensor as claimed in claim 1, wherein said first electrodes have generally the shape of an equal-sided triangle and wherein said stud portions of the conductive track that contact the border portions of said first electrodes extend from a tip of said triangle.

14. The pressure sensor as claimed in claim 1, wherein said second electrodes have generally the shape of an equal-sided triangle and wherein said stud portions of the conductive track that contact the border portions of said second electrode extend from a tip of said triangle.

15. A pressure sensor as claimed in claim 1, further comprising a flexible multilayer film structure, wherein the pressure sensor further comprises a trough-shaped receptacle for an electronic control module, said receptacle comprising in its interior a plurality of connection pins for interfacing said pressure sensor with said electronic control module.

16. The pressure sensor as claimed in claim 15, wherein said receptacle is arranged in an opening provided in said flexible multilayer film structure.

17. The pressure sensor as claimed in claim 16, wherein said receptacle comprises a bottom part and a top part, said bottom part and said top part being assembled with each other so as to squeeze between each other a border of said opening in said multilayer film structure and thus securing said multilayer film structure to said receptacle.

18. The pressure sensor as claimed in claim 15, wherein said receptacle comprises a bottom part and a top part, said bottom part and said top part being assembled with each other so as to squeeze between each other a border of said opening in said multilayer film structure and thus securing said multilayer film structure to said receptacle.

* * * * *